United States Patent
Fry

(10) Patent No.: US 6,254,836 B1
(45) Date of Patent: Jul. 3, 2001

(54) SCENT DISPENSING AIR FRESHENERS

(76) Inventor: Debbi Fry, 56925 Yucca Trail, suite A, Yucca Valley, CA (US) 92284

( * ) Notice: Subject to any disclaimer, the term of this patent is extended or adjusted under 35 U.S.C. 154(b) by 0 days.

(21) Appl. No.: 09/243,581

(22) Filed: Feb. 3, 1999

(51) Int. Cl.$^7$ ..................................................... A62B 7/08
(52) U.S. Cl. ........................... 422/124; 239/34; 239/53; 239/56; 239/57; 239/211; 422/122; 422/123
(58) Field of Search .................................. 422/122, 123, 422/124, 4, 5; 239/34, 53, 56, 57, 211

(56) References Cited

U.S. PATENT DOCUMENTS

| | | | |
|---|---|---|---|
| 4,477,414 | * 10/1984 | Muramoto et al. | 422/125 |
| 4,869,407 | * 9/1989 | Booth, Jr. et al. | 222/633 |
| 5,334,361 | * 8/1994 | Rafaelides et al. | 422/305 |
| 5,422,078 | * 6/1995 | Colon | 422/123 |

* cited by examiner

Primary Examiner—Krisanne Thornton
(74) Attorney, Agent, or Firm—Michael I. Kroll

(57) ABSTRACT

The present invention 10 discloses a device for an air freshener for use by hanging in an automobile 12 or other location made in a variety of native American shapes 18, 26, 28 and 30. The present invention 10 is provided with a circular bulb 24 on its backside and further the device contains an amount of absorbent material 34 held in a recessed space 35 in its body 10 for holding liquid scented oil 48. The scent can be dispersed into the atmosphere by selectively depressing and releasing the bulb 24 so that an amount of air is dispelled through scent apertures 20 into the air space surrounding the air freshener of the present invention 10. In an alternative embodiment, the bulb 24 is threaded 40 into the air freshener 10 and contains an amount of absorbent material 44 whereby scent oil 48 is placed directly on the absorbent material 44 therein which then can be displaced into the air surrounding the air freshener 10 by pressing on the bulb 24 with the scent passing through said air apertures 20.

5 Claims, 11 Drawing Sheets

SCENT DISPENSING AIR FRESHENERS

BACKGROUND OF THE INVENTION

1. Field of the Invention

The present invention relates generally to air fresheners and more specifically to hanging car air fresheners conforming to specific native American symbols and having an amount of liquid scent contained within a chamber having an absorbent material for the retention of said liquid scent and wherein said chamber is substantially hermetically sealed whereby said scent can be retained for an extended period of time being selectively released by depressing a bulb having an amount of scent containing air which passes through said scent containing material before being expelled through a plurality of scent egress apertures and whereupon release of the bulb said scent egress apertures function as atmospheric air in draft apertures bringing said scent containing chamber into equilibrium with atmospheric pressure whereby said bulb and said process can be continued until the desired result has been achieved and furthermore said egress/in draft apertures can be constructed in such a manner as to be self sealing during atmospheric equilibrium.

In addition another embodiment is provided wherein said bulb is threaded into said air freshener whereby said bulb can be removed and a selectable amount of scent can be added to said scent containing material before reattaching said bulb thereby extending the life of a favored air freshener and enhancing the scope of scents which can be deposited therein.

2. Description of the Prior Art

There are other air fresheners designed to emit scent. Typical of these is U.S. Pat. No. 4,595,564 issued to Spector et al. on Jun. 17, 1986.

Another patent was issued to Traylor et al. on Jan. 9, 1996 as U.S. Pat. No. Des. 366,108. Yet another U.S. Pat. No. Des. 387,853 was issued to Little on Dec. 16, 1997 and still yet another was issued on Sep. 5, 1995 to Clayton as U.S. Pat. No. Des. 362,057.

U.S. Pat. No. 4,595,564

Inventor: Donald Spector et al.

Issued: Jun. 17, 1986

A cartridge-type aroma percolator for wafting fragrance into the atmosphere at a relatively high rate. The percolator includes a cylindrical container having a vented cap and a base provided with a raised hub housing an electric heater. Telescopically inserted into the container is a replaceable cartridge having a can whose base has a reentrant socket that complements and receives the hub. Placed adjacent the upper end of the can is a liquid-permeable toroidal insert incorporating a pad of porous material, the insert defining therebelow a chamber having a pool therein of an aqueous solution of a volatile liquid fragrance. A tube coaxial with the can extends through the hollow core of the barrier, the tube inlet being immersed in the pool adjacent the socket, the tube outlet being above the barrier. When the heater is energized, the solution in the region of the socket is caused to boil to produce a head of pressurized gas above the pool, forcing the liquid to rise in the tube and to be discharged from the outlet to shower onto the insert whereby the liquid percolates through the pad before returning to the chamber. An aromatic vapor emitted from the pad is wafted into the atmosphere through the vented cap of the percolator. A removable cover means is provided for hermetically sealing said can, and for storing the contents thereof, while the cartridge is not in use.

U.S. Pat. No. Des. 366,108

Inventor: Melissa J. Traylor

Issued: Jan. 9, 1996

This United States Patent discloses an ornamental design for a hanging air freshener as illustrated in the drawings of the patent.

U.S. Pat. No. Des. 387,853

Inventor: Fester G. Little

Issued: Dec. 16, 1997

This United States Patent discloses an ornamental design for an air freshener housing as illustrated in the drawings of the patent.

U.S. Pat. No. Des. 362,057

Inventor: Herbert S. Clayton

Issued: Sep. 5, 1995

This United States Patent discloses an ornamental design for an eagle in flight freshener as illustrated in the drawings of the patent.

While these air fresheners may be suitable for the purposes for which they were designed, they would not be as suitable for the purposes of the present invention, as hereinafter described.

SUMMARY OF THE PRESENT INVENTION

The present invention discloses a device for an air freshener for use by hanging in an automobile or other location made in a variety of native American shapes. The present invention is provided with a circular bulb on its backside and further the device contains an amount of absorbent material held in a recessed space in its body for holding liquid scented oil. The scent can be dispersed into the atmosphere by selectively depressing and releasing the bulb so that an amount of air is dispelled through scent apertures into the air space surrounding the air freshener of the present invention. In an alternative embodiment, the bulb is threaded into the air freshener and contains an amount of absorbent material whereby scent oil is placed directly on the absorbent material therein which then can be displaced into the air surrounding the air freshener by pressing on the bulb with the scent passing through said air apertures.

A primary object of the present invention is to provide air fresheners in the form of native American symbols.

Another object of the present invention is to provide the aforementioned air fresheners using one of the following scents, sweet grass, cedar, lavender and sage.

Yet another object of the present invention is to provide air fresheners with means for discharging a reservoir of the original scent.

Still yet another object of the present invention is to provide air fresheners having a chamber for storing an amount of scent.

Yet another object of the present invention is to provide air fresheners having a bulb for discharging an amount of stored scent.

Additional objects of the present invention will appear as the description proceeds.

The present invention overcomes the shortcomings of the prior art by providing hanging air fresheners conforming to specific native American symbols and having an amount of liquid scent contained within a chamber having means for selectively releasing said scent into the atmosphere by depressing an integral bulb ejecting an amount of scent through a plurality of scent egress apertures and upon release of the bulb said scent egress apertures function as atmospheric air in draft apertures bringing said scent containing chamber into equilibrium with atmospheric pressure whereby said bulb and said process can be continued until the desired result has been achieved.

In addition another embodiment is provided wherein said bulb is threaded into said air freshener whereby said bulb can be removed and a selectable amount of scent can be added too said scent containing material before reattaching said bulb thereby extending the life of a favored air freshener and enhancing the scope of scents which can be deposited therein.

The foregoing and other objects and advantages will appear from the description to follow. In the description reference is made to the accompanying drawings, which form a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawings in which.

LIST OF REFERENCE NUMERALS

Figure 1:
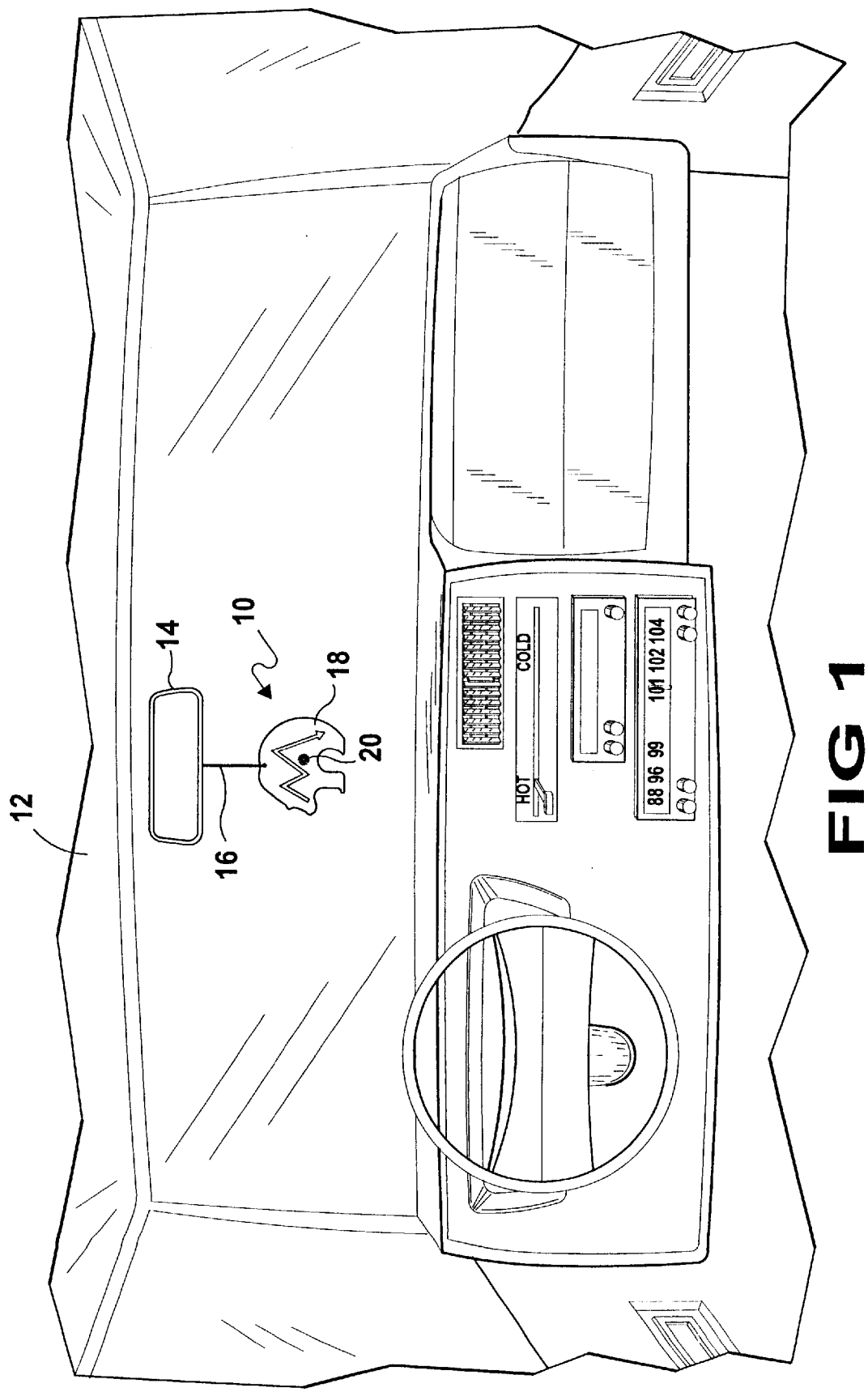
FIG. 1 is a perspective view of the present invention in use. Shown is a rearview mirror having attached thereupon a hanging air freshener in the form of a bear.

With regard to the reference numerals used, the following numbering is used throughout the various figures.

10 present invention
12 automobile
14 rear view mirror
16 string
18 bear
20 scent apertures
22 string hole
24 bulb
25 removable edge of bulb
26 gecko shape
28 kokopelli shape
30 eagle shape
32 air chamber
34 absorbent material
35 recess in body
36 attachment means
40 male threaded member
42 female threaded recess
44 absorbent material
46 air chamber
48 scented oil
50 bottle of scent

DESCRIPTION OF THE PREFERRED EMBODIMENT(S)

Turning now descriptively to the drawings, in which similar reference characters denote similar elements throughout the several views, FIGS. 1 through 11 illustrate the present invention being an air freshener made in various native American shapes.

Turning to FIG. 1, therein is shown a perspective view of the present invention 10 in operative connection. Therein is shown an automobile 12 along with a rear view mirror 14 upon which the present invention 10 is hung by a string 16. The present invention 10 is shown more particularly in the shape of a bear 18. Scent apertures 20 can also be seen.

Figure 2:
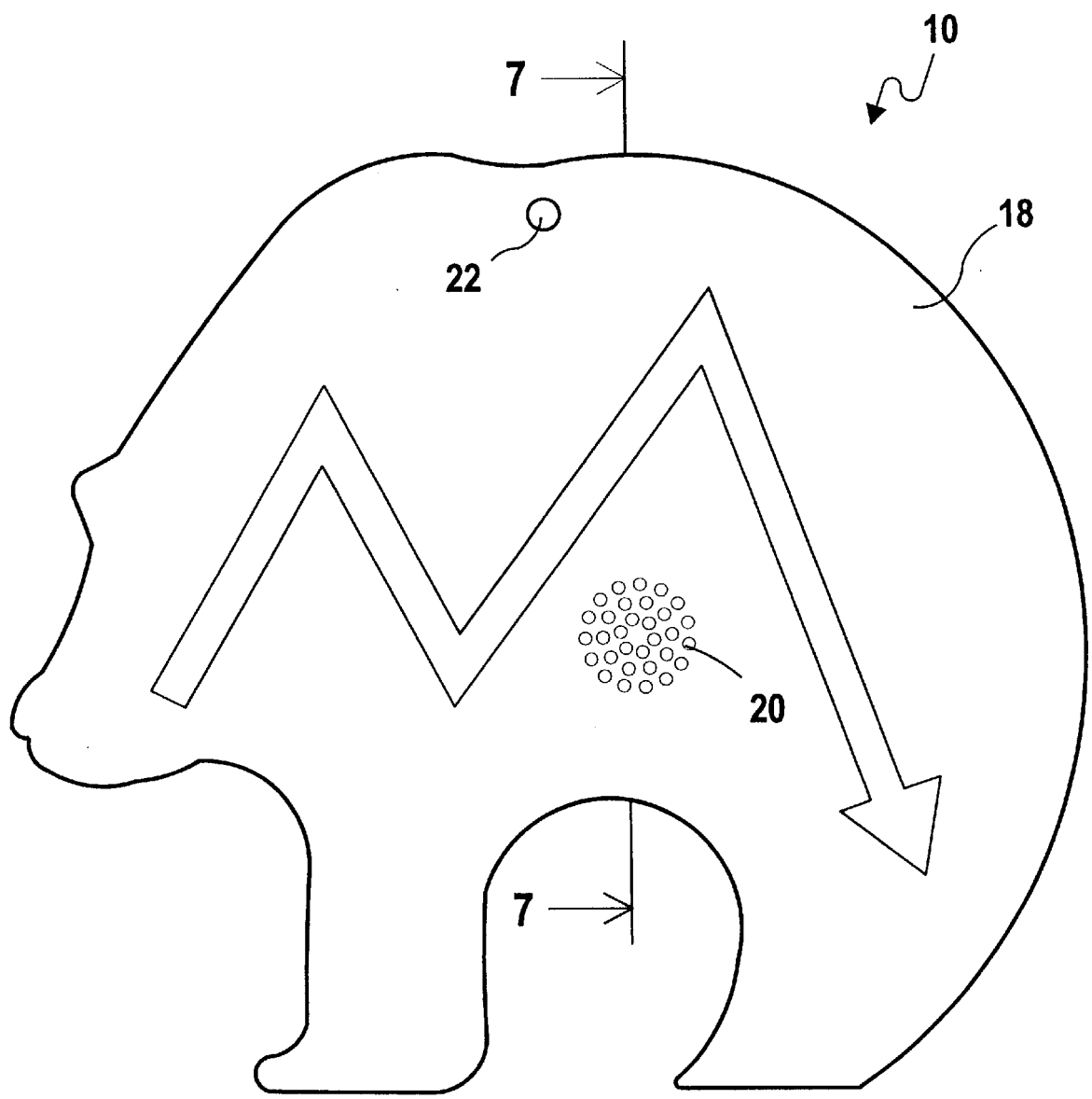
FIG. 2 is an enlarged front elevational view of one form of the preferred embodiment of the present invention. Shown is an air freshener in the form of a bear having a plurality of apertures for dispensing an amount of the source scent.

Turning to FIG. 2, therein is shown an enlarged front elevational view of the bear form of the preferred embodiment of the present invention 10. Shown is an air freshener 10 in the form of a bear 18 having a plurality of apertures 20 for dispensing an amount of the air freshening scent into the air surrounding the air freshener. Also shown is an aperture 22 through which a string or like can be used to attach the present invention 10 to a rear view mirror or like of an automobile or other location.

Figure 3:
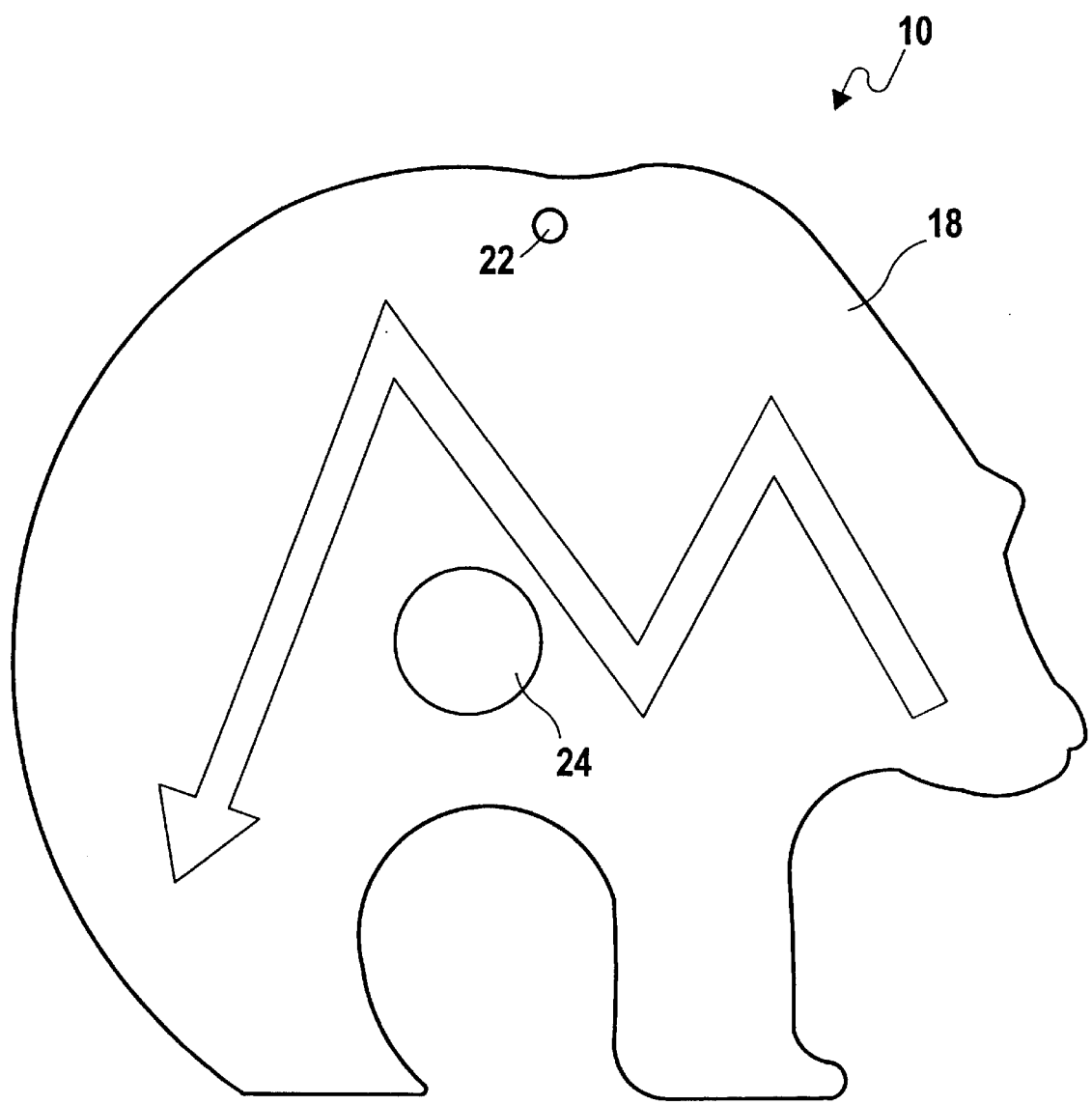
FIG. 3 is an enlarged back elevational view, taken from FIG. 1 as indicated, showing the bulb providing means for dispensing an amount of the source scent into the atmosphere.

Turning to FIG. 3, therein is shown an enlarged back elevational view, taken from FIG. 1 as indicated, showing a flexible bulb 24 which bulb provides a means for dispensing an amount of the source scent into the atmosphere surrounding the air freshener of the present invention 10. The scent is dispelled from the present invention 10 by the user pressing on the flexible bulb made of rubber or like material. It can be seen that the bulb 24 is circular in shape and is attached by means to the back side of the present invention 10.

Figure 4:
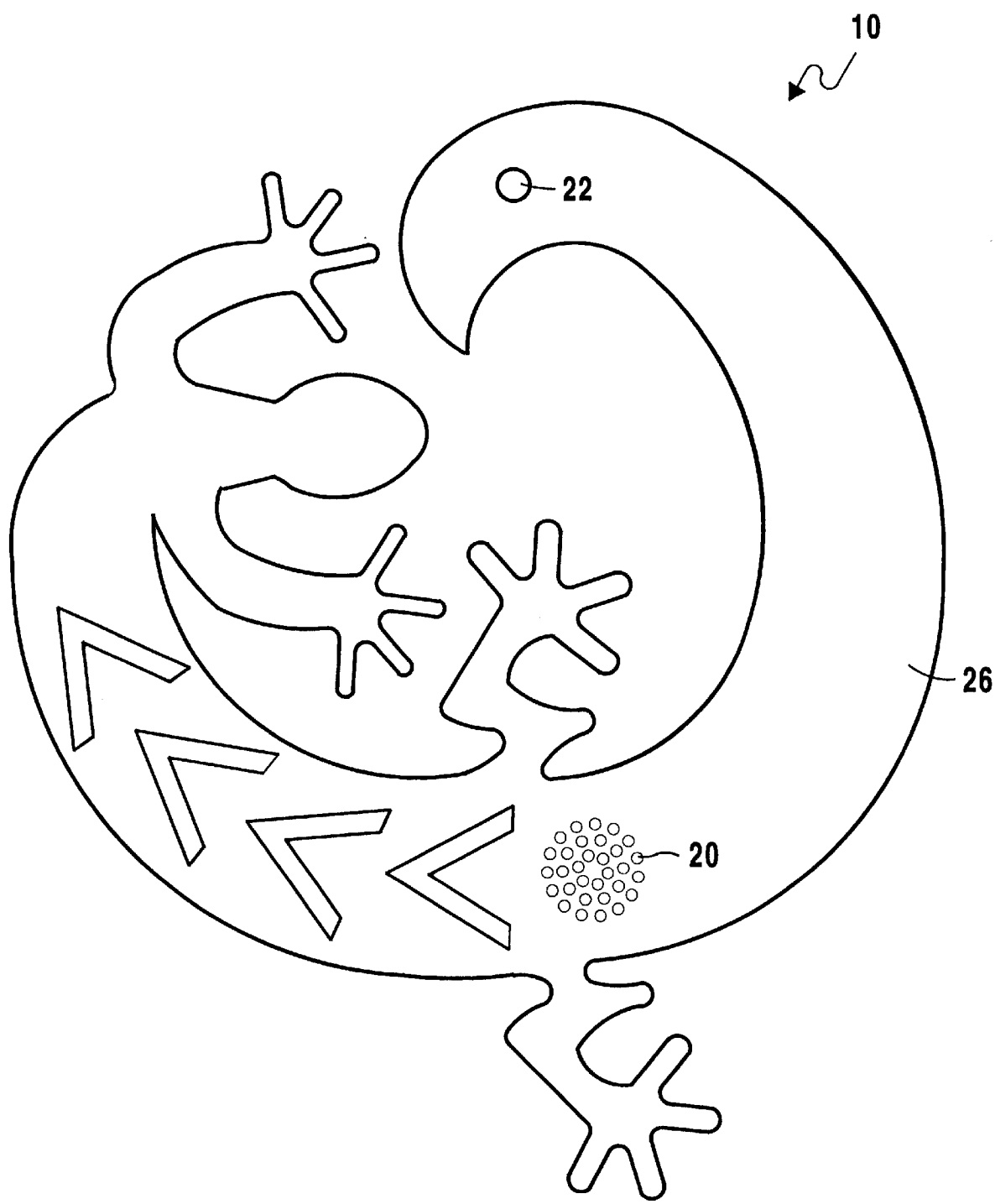
FIG. 4 is an enlarged view of another form of the preferred embodiment of the present invention. Shown is an air freshener in the form of a gecko having a plurality of apertures for dispensing an amount of the source scent.

Turning to FIG. 4, therein is shown an enlarged view of an alternative form of the preferred embodiment of the present invention 10. Shown is the air freshener 10 in the form of a gecko 26 having a plurality of apertures 20 for dispensing an amount of the source scent. Also shown is a hole 22 for attachment of a string for holding the present invention as previously discussed.

Figure 5:
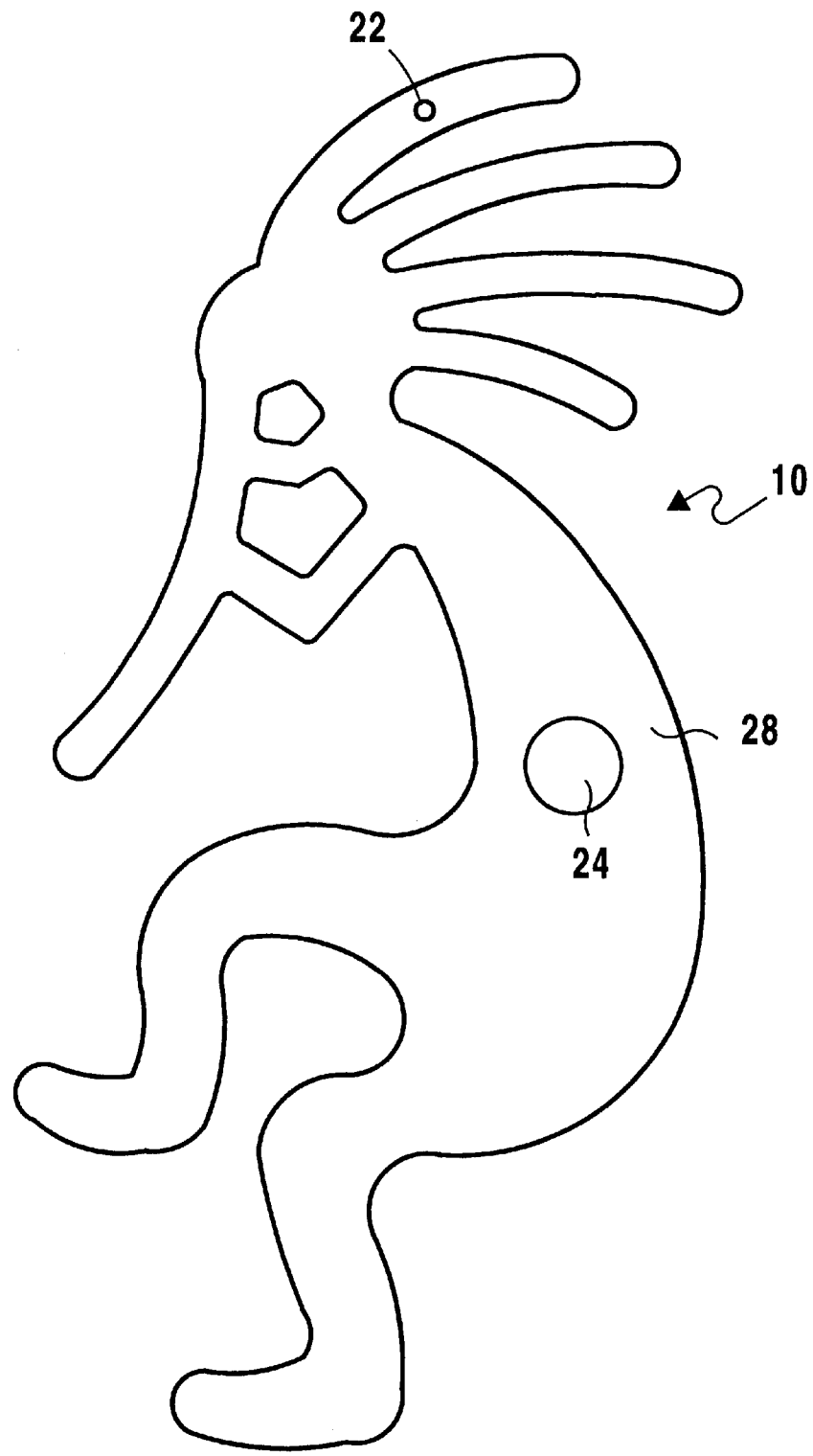
FIG. 5 is an enlarged rear elevational view of another form of the preferred embodiment of the present invention. Shown is an air freshener in the form of a kokopelli having a bulb providing means for dispensing an amount of the source scent into the atmosphere.

Turning to FIG. 5, therein is shown an enlarged rear elevational view of another form of the preferred embodiment of the present invention 10. Shown is an air freshener 10 in the form of a kokopelli 28 having a bulb 24 providing means for dispensing an amount of the source scent into the atmosphere surrounding the air dispenser 10. Also shown is the string hole 22.

Figure 6:
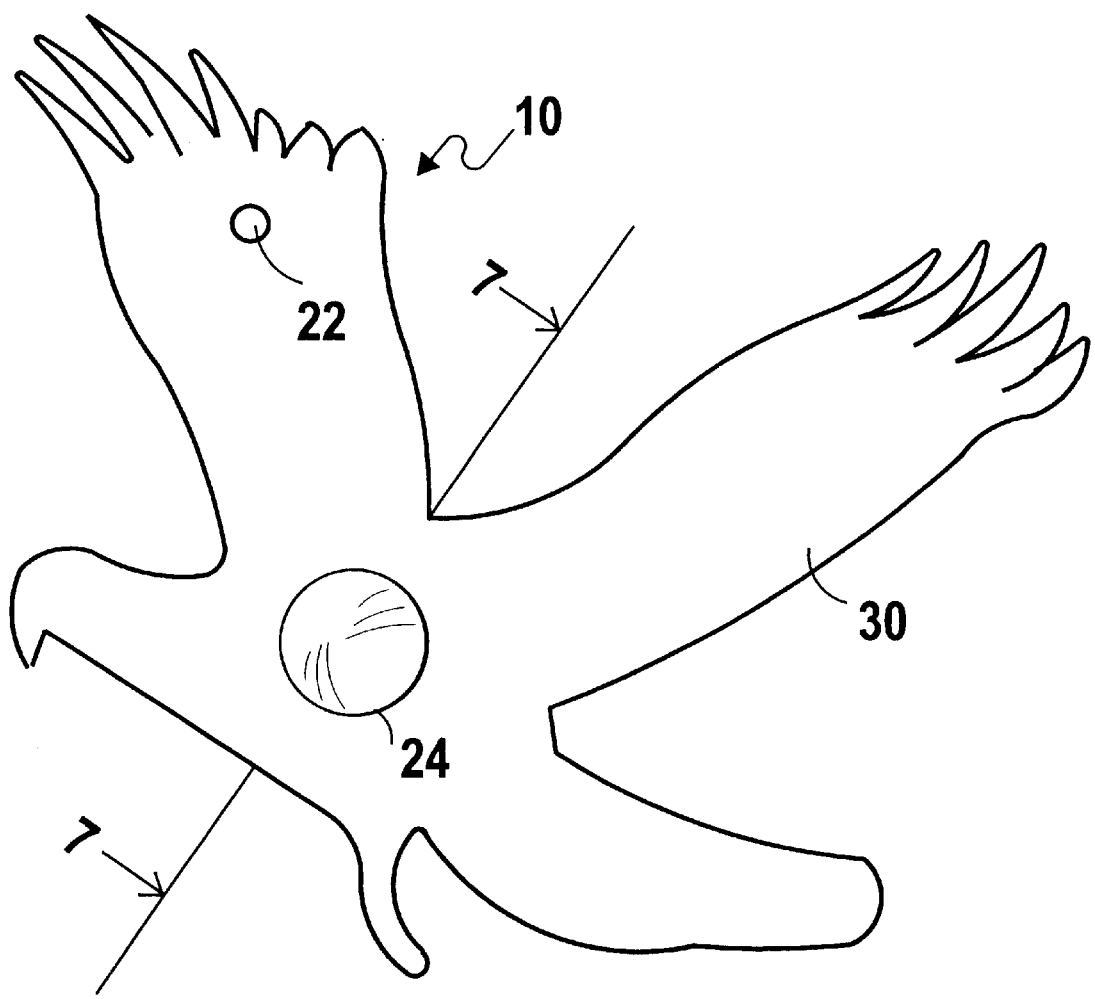
FIG. 6 is an enlarged rear elevational view of another form of the preferred embodiment of the present invention. Shown is an air freshener in the form of an eagle having a bulb providing means for dispensing an amount of the source scent into the atmosphere.

Turning to FIG. 6, therein is shown an enlarged rear elevational view of another form of the preferred embodiment of the present invention 10. Shown is an air freshener in the form of an eagle 30 having a bulb 24 providing means for dispensing an amount of the source scent into the atmosphere surrounding the air freshener 10. Also shown is a string hole 22 therein.

Figure 7:
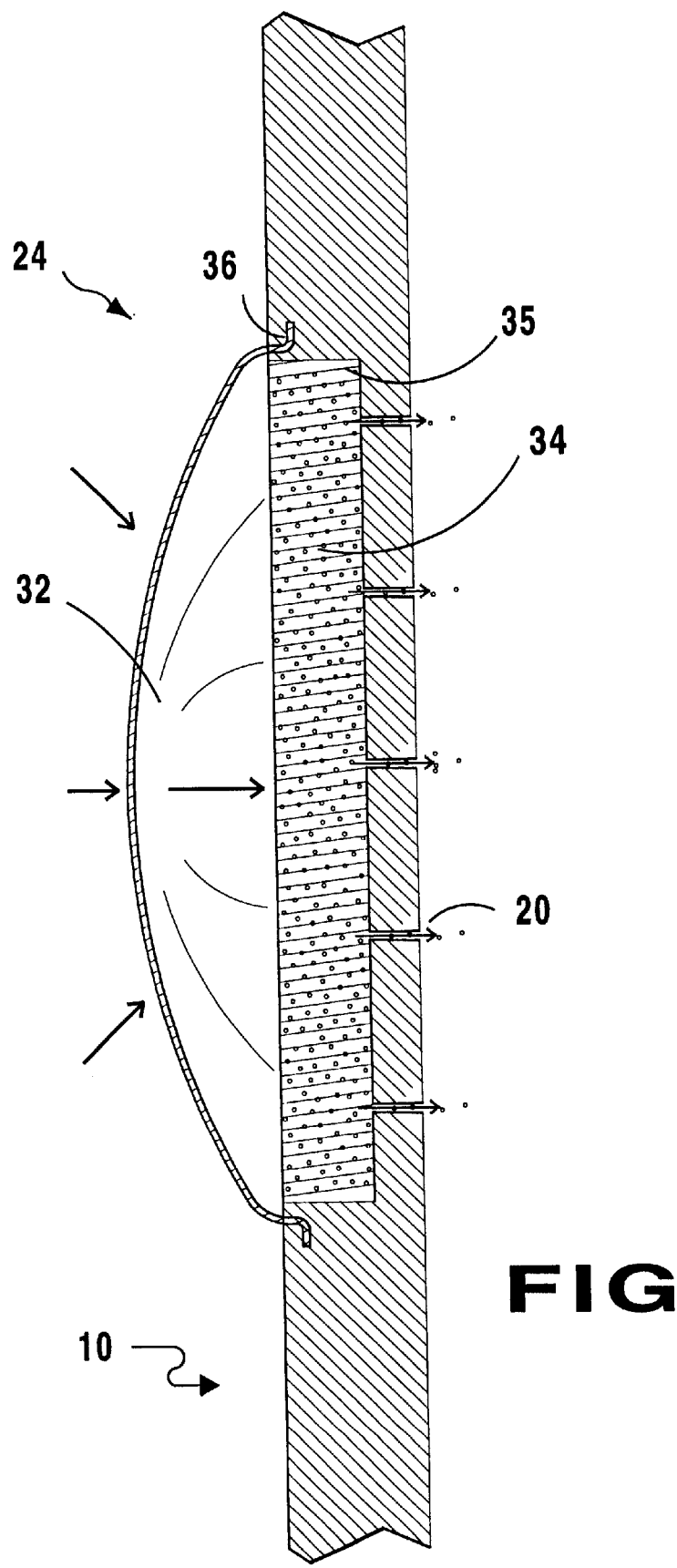
FIG. 7 is a cross sectional view, taken from FIG. 2 as indicated, showing the bulb having a chamber with an amount of scented air and having an absorbent material for retaining the liquid scent and a number of apertures for dispensing said scent into the atmosphere.

Turning to FIG. 7, therein is shown a cross-sectional view taken from FIG. 2 as indicated, showing the bulb 24 of the present invention 10 having an air chamber 32 contained therein containing an amount of scented air and further having an absorbent material 34 for retaining the liquid scent therein. Also shown are a number of apertures 20 for dispensing said scent into the atmosphere. It can be seen that the bulb 24 is connected to the present invention 10 around its circumferential periphery 36. Means 36 of connecting the bulb 24 to the present invention 10 in the standard manner can be utilized. Also shown is the recess 35 in the body of the present invention 10 wherein the absorbent material 34 is placed. The absorbent material 34 could be made of foam, paper, or fabric like material in the standard manner. It should be clear that the scent can be selectively released by depressing the bulb 24 having an amount of scent containing air which passes through said scent containing material 34 before being expelled through a plurality of scent egress apertures 20 and whereupon release of the bulb 24 occurs said scent egress apertures 20 function as atmospheric air indraft apertures 20 bringing said scent containing chamber into equilibrium with atmospheric pressure whereby said bulb 24 and said process can be continued until the desired result has been achieved.

Figure 8:
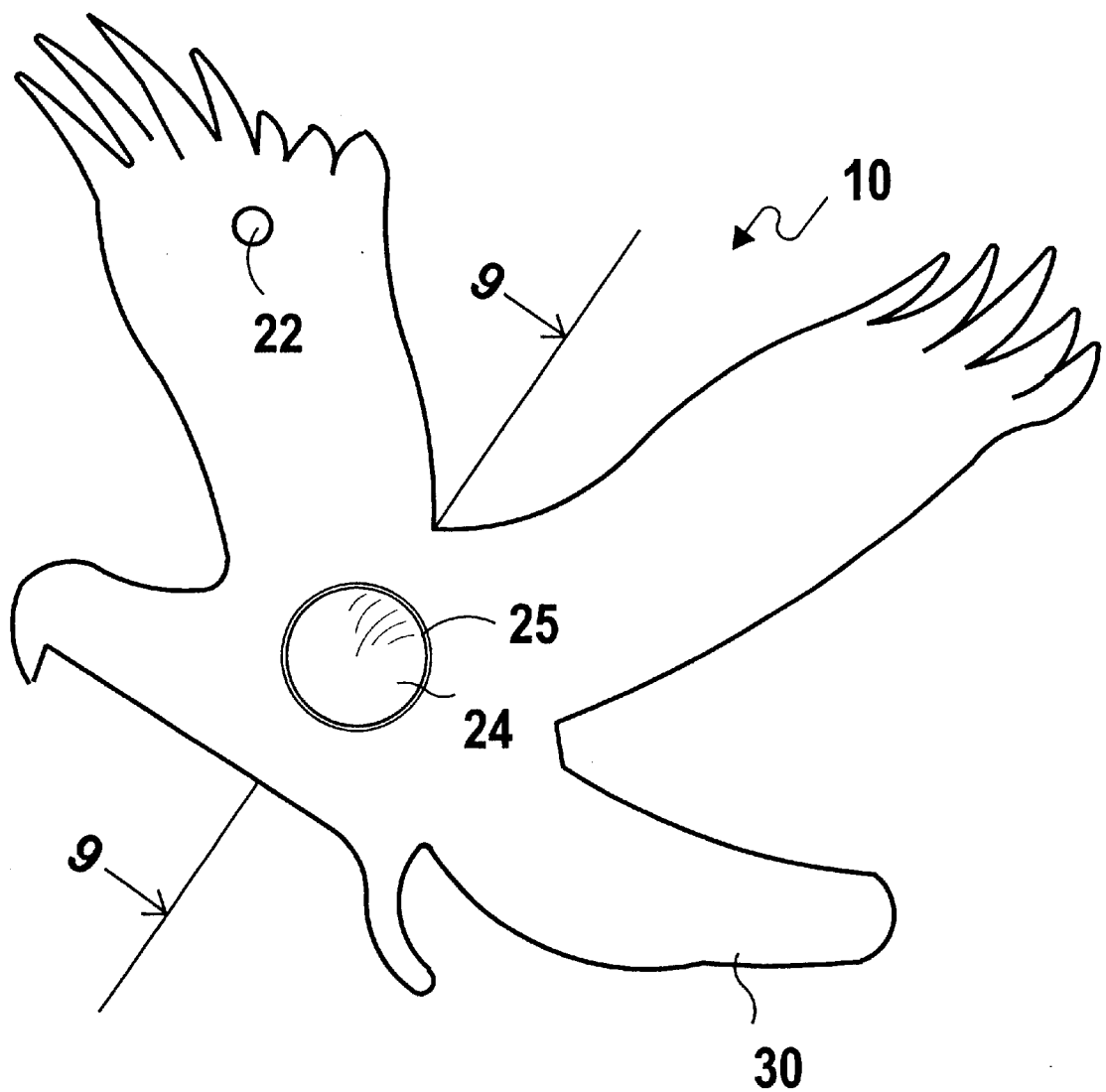
FIG. 8 is an enlarged rear elevational view of another embodiment of the present invention. Shown is an air freshener in the form of an eagle having a bulb providing means for dispensing an amount of the source scent into the atmosphere and being removable for the purposes of adding additional scent material.

Turning to FIG. 8, therein is shown an enlarged rear elevational view of another embodiment of the present invention 10. Shown is an air freshener in the form of an eagle 30 having a bulb 24 providing means for dispensing an amount of the source scent into the atmosphere surrounding the air freshener 10 and being removable at its edge 25 for the purpose of adding additional scent material. Also shown therein is a string hole 22.

Figure 9:
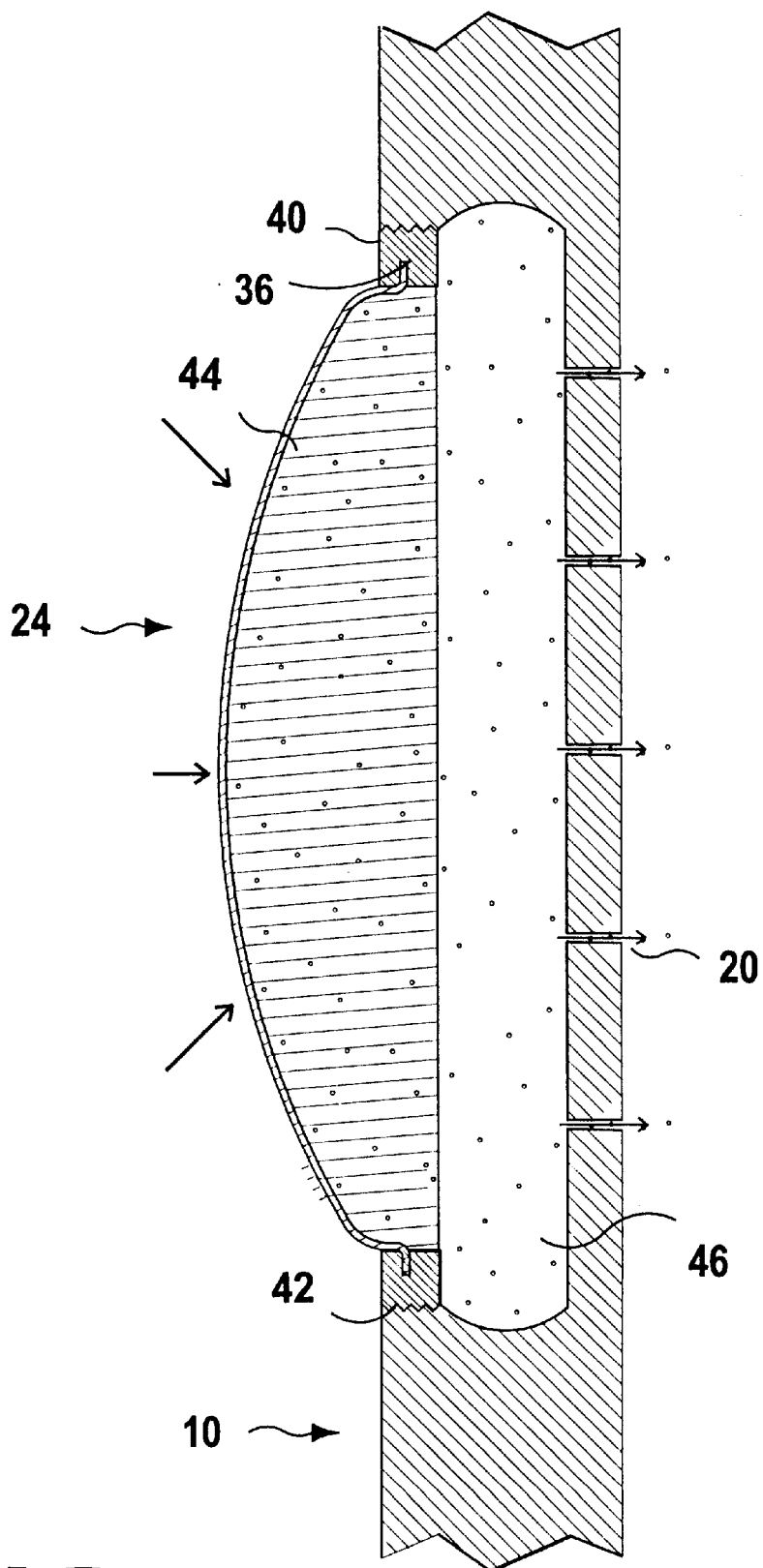
FIG. 9 is a cross sectional view, taken from FIG. 8 as indicated, showing the threaded bulb member having an amount of absorbent material attached thereto and having a chamber with an amount of scented air therein and a number of apertures for dispensing said scent into the atmosphere.

Turning to FIG. 9, therein is shown a cross-sectional view taken from FIG. 8 as indicated, showing the threaded bulb member 24 having a threaded member 40 located around the circumference at its base acting as a threaded male member 40 for being attached to the present invention 10 by being threaded into a female threaded recess 42 located therein. It can be seen that the threaded male member 40 is attached to and threaded into the female member 42 which is formed into and recessed into the body of the present invention 10. It can be seen that in this embodiment the bulb member 24 has an amount of absorbent material 44 contained therein and that the body of the present invention 10 contains an air chamber 46 containing an amount of scented air therein and a number of apertures 20 for dispensing said scent into the atmosphere. Attachment means 36 are shown for attaching the bulb 24 to the male threaded member 40 in the standard manner.

Figure 10:
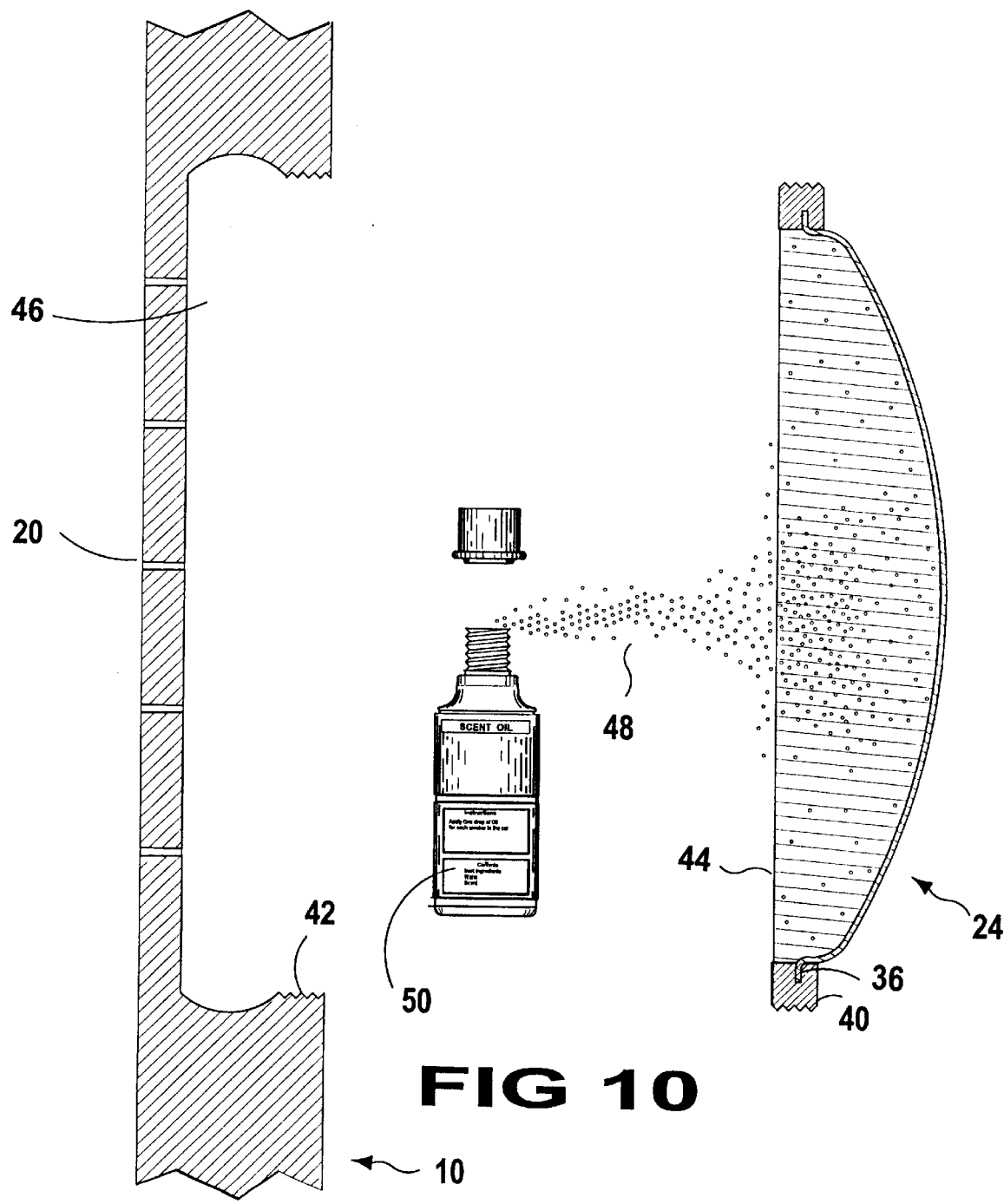
FIG. 10 is a cross sectional view, taken from FIG. 9 as indicated, showing the threaded bulb member removed from the air freshener and an amount of scent being added to the absorbent material of the bulb from a bottle of liquid scent.

Turning to FIG. 10, therein is shown a cross-sectional view, taken from FIG. 9 as indicated, showing the bulb 24 along with its male threaded perimeter member 40 containing the absorbent material 44. It can be seen that an amount of scented oil 48 is being added to the absorbent material 44 of the bulb 24 from a bottle of liquid scented oil material 50. Also shown is the threaded female member 42 of the present invention 10 along with the cavity of the air chamber 46 and the apertures for the air 20. Attachment means 36 is also shown.

Figure 11:
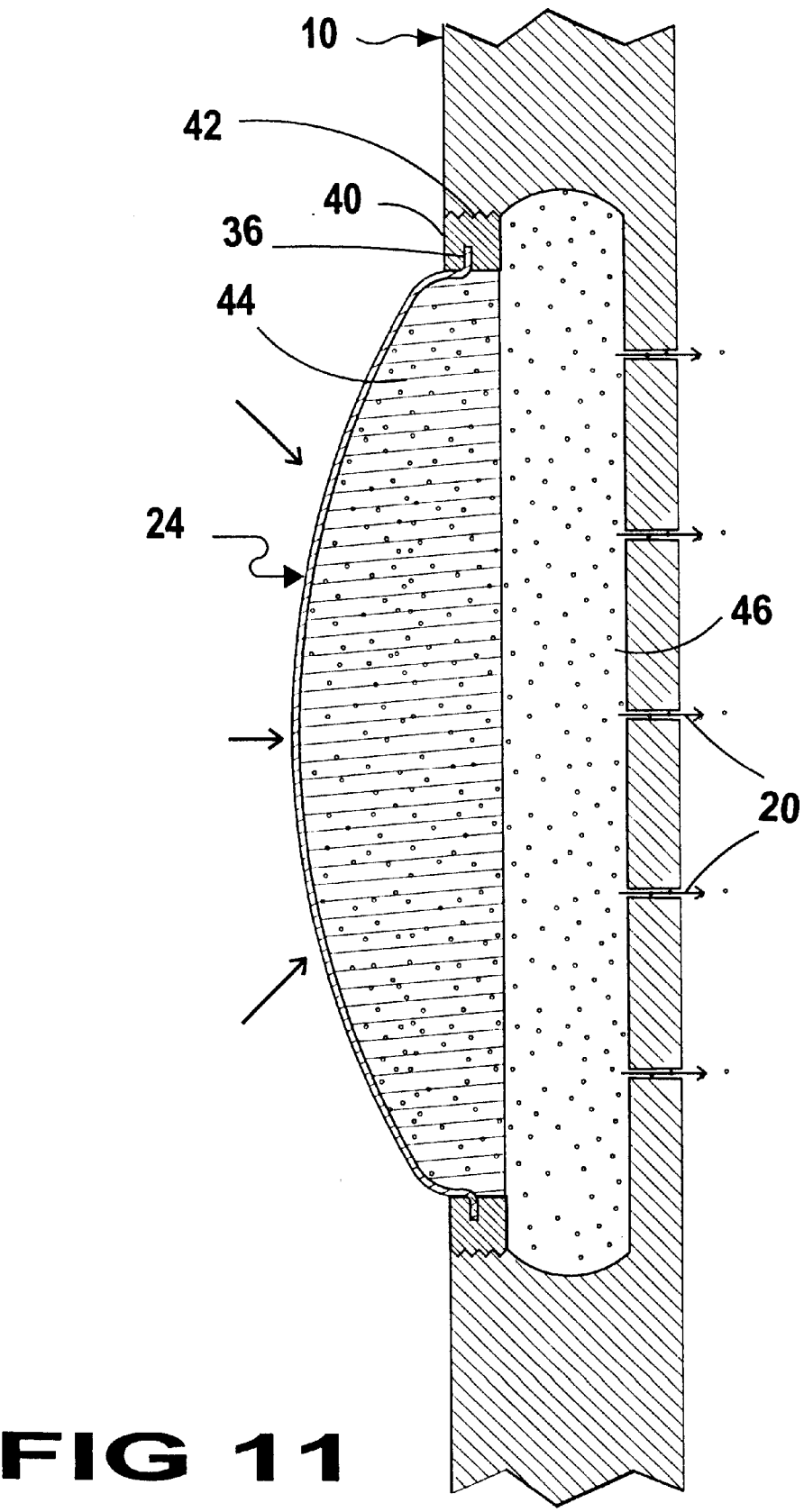
FIG. 11 is a diagrammatic cross sectional view of the Figure shown in FIG. 8 showing the threaded bulb member having an amount of absorbent material attached thereto with an amount of additional scent therein and having a chamber with an amount of scented air therein and a number of apertures for dispensing said scent into the atmosphere.

Turning to FIG. 11, therein is shown a cross-sectional view taken from FIG. 8 as indicated, showing the threaded bulb member 24 having a threaded male member 40 located around the circumference of its base for being attached to the present invention 10 having a threaded female recess 42 located therein. It can be seen that the threaded male member 40 is attached to and threaded into the female member 42 which is formed into the body of the present invention 10. It can be seen that in this embodiment the bulb member 24 has an amount of absorbent material 44 contained therein along with an air chamber 46 containing an amount of scented air therein and a number of apertures 20 for dispensing said scent into the atmosphere. Attachment means 36 is also shown.

What is claimed is new and desired to be protected by Letters Patent is set forth in the claims:

1. An apparatus for an air freshener, comprising:
   a) a body having a front side and a rear side, with apertures on the front side and a recess in the rear side so that said apertures extend directly from said recess through the front side;
   b) said body having a threaded opening on said rear side leading into said recess;
   c) an annular threadable member engaging said threaded opening;
   d) said threadable member having a smooth, flexible bulb with a rim thereof imbedded in said threadable member and bulging outwardly from said rear side forming a pocket facing said recess, with an absorbent pad containing scent oil filling said pocket and scent filling said recess;

e) said flexible bulb upon being pressed releases scent out from said recess through said apertures;

f) said threadable member and bulb being removable to permit recharging of said pad with scent oil; and g) means for suspending said body within a vehicle for discharge as needed of scent.

2. The apparatus of claim 1, wherein said body is in the shape of a bear.

3. The apparatus of claim 1, wherein said body is in the shape of a gecko.

4. The apparatus of claim 1, wherein said body is in the shape of a Kokopelli.

5. The apparatus of claim 1, wherein said body is in the shape of an eagle.

* * * * *